United States Patent
Pitfield et al.

(10) Patent No.: US 6,572,663 B1
(45) Date of Patent: Jun. 3, 2003

(54) METHOD FOR PRODUCING HAIR COLORING PREPARATIONS WITH IMPROVED VISCOSITY

(75) Inventors: Adrian Pitfield, Brombachtal-Kirchbrombach (DE); Heribert Lorenz, Gross Bieberau (DE); Frank Golinski, Darmstadt (DE); Joerg Kahre, Leichlingen (DE); Thomas Foerster, Erkrath (DE); Markus Sumser, Herne (DE); Armin Wadle, Erkrath (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 0 days.

(21) Appl. No.: 09/581,394

(22) PCT Filed: Dec. 4, 1998

(86) PCT No.: PCT/EP98/07903

§ 371 (c)(1), (2), (4) Date: Oct. 13, 2000

(87) PCT Pub. No.: WO99/30676

PCT Pub. Date: Jun. 24, 1999

(30) Foreign Application Priority Data

Dec. 13, 1997 (DE) .......................... 197 55 491

(51) Int. Cl.$^7$ ................................. A61K 7/13
(52) U.S. Cl. ................... 8/405; 8/435; 8/552
(58) Field of Search ........................ 8/405, 406, 407, 8/408, 409, 435, 410, 412, 413, 414, 415, 416, 10.1, 101; 424/70, 71, 78, 401; 510/122, 127, 100, 156

(56) References Cited

U.S. PATENT DOCUMENTS

| 4,172,887 A | | 10/1979 | Vanlerberghe et al. ......... 424/70 |
| 4,184,843 A | | 1/1980 | Baumann ..................... 8/10.1 |
| 5,160,733 A | * | 11/1992 | Berthiaume et al. |
| 5,480,459 A | | 1/1996 | Mager et al. ................. 8/408 |
| 5,609,651 A | | 3/1997 | Mager et al. ................. 424/70 |
| 5,693,317 A | * | 12/1997 | Reich et al. .............. 424/70.15 |
| 5,985,255 A | * | 11/1999 | Vanlerberghe et al. ... 424/70.28 |

FOREIGN PATENT DOCUMENTS

| CH | 188 988 | 4/1937 |
| DE | 27 36 067 | 3/1978 |
| DE | 20 24 051 | 5/1986 |
| DE | 1 165 574 | 3/1994 |
| DE | 43 32 965 | 3/1995 |
| DE | 44 11 557 | 10/1995 |
| EP | 0 687 206 | 9/1994 |
| FR | 2 252 840 | 12/1978 |
| GB | 962 919 | 7/1964 |
| GB | 1 333 475 | 10/1973 |
| WO | WO93/23006 | 11/1993 |

OTHER PUBLICATIONS

Surfactants in Consumer Products, (1987), pp. 54–124.
J. Falbe, U. Hasserodt, *Katalysatoren Tenside und Mineroeladditive*, Georg Thieme Verlag Stuttgart 1978, pp. 123–217 (1984).
H. Eicke, *Mikroemulsionen—eine wissenschaftliche und anwendungstechnische Fundgrube?*, SÖFW–Journal, 118, pp. 311–315 (1992).
T. Foerster, *Neuartige Koerperpflegemittel auf Basis von Mikroemulsionen mit Alkylpolyglykosiden*, SÖFW–Journal, 122, pp. 746–753 (1996).
*Kosmetische Faerbemittel*, Farbstoffkommission der Deutschen Forschungsgemeinschaft, pp. 81–106 (1984).
P. Finkel, *Formulierung kosmetischer Sonnenschutzmittel*, SÖFW–Journal 122, pp. 543–546 (1996).

* cited by examiner

*Primary Examiner*—Lorna M. Douyon
*Assistant Examiner*—Eisa Elhilo
(74) *Attorney, Agent, or Firm*—John E Drach; Steven J Trzaska

(57) ABSTRACT

A process for making a hair dye preparation involving: (a) providing an aqueous surface-active fatty alcohol dispersion containing: (i) a fatty alcohol; and (ii) a surfactant; (b) providing an oil component; (c) providing a hair dye component; and (d) combining (a)–(c), at a temperature of from 18 to 25° C., to form the hair dye preparation.

14 Claims, No Drawings

METHOD FOR PRODUCING HAIR COLORING PREPARATIONS WITH IMPROVED VISCOSITY

BACKGROUND OF THE INVENTION

1. Field of the Invention

The invention relates to a method for the cold-production of hair coloring preparations, preferably coloring creams, in which surface-active fatty alcohol dispersions are used.

For the production of hair coloring preparations, such as, for example, creams of the oil-in-water type, fatty alcohols are normally used to adjust the viscosity. The emulsions are prepared here by the hot-method, i.e. the constituents are mixed above the melting point of the highest-boiling component and then slowly cooled with intensive homogenization. For reasons of efficiency, however, it is desirable to prepare such preparations by a cold method, for example using known PIT or microemulsion technology. However, in this connection, a problem arises inasmuch as adjustment of high viscosities is possible only with very great difficulty, particularly when lamellar gels are prepared using fatty alcohols.

Consequently, the object of the invention was to provide a method for the cold-production of hair coloring preparations, in particular creams of the O/W type, which can also be used to produce lamellar gels having particularly good storage stability.

2. Description of the Invention

The invention provides a method for producing hair coloring preparations with improved viscosity, in which aqueous surface-active fatty alcohol dispersions are stirred up with oil components and hair dyes in the cold.

Surprisingly, we have found that it is also possible to prepare O/W cream preparations for the coloring of hair by a cold method if surface-active fatty alcohol dispersions, preferably fatty alcohol microdispersions, are used to adjust the consistency. The resulting compositions are in the form of lamellar gels which are notable for particularly high stability, even during storage above room temperature.

Fatty Alcohols

The dispersions to be used for the purposes of the method according to the invention may comprise fatty alcohols of the formula (I)

$$R^1OH \qquad (I)$$

in which $R^1$ is a linear or branched, saturated or unsaturated alkyl radical having 6 to 30 carbon atoms. Typical examples are caproic alcohol, caprylic alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachidyl alcohol, gadoleyl alcohol, behenyl alcohol, erucyl alcohol and brassidyl alcohol, and technical-grade mixtures thereof, which are produced, for example, during the high-pressure hydrogenation of technical-grade methyl esters based on fats or oils or aldehydes from the Roelen oxo synthesis, and as monomer fraction during the dimerization of unsaturated fatty alcohols. Preference is given to technical-grade fatty alcohols having 12 to 18 carbon atoms, such as, for example, coconut, palm, palm kernel, cetearyl or tallow fatty alcohol. The proportion of fatty alcohols in the dispersions can here be 5 to 50% by weight and preferably 25 to 40% by weight.

Surfactants

The fatty alcohol dispersions to be used for the purposes of the method according to the invention may comprise anionic, nonionic, cationic and/or amphoteric or zwitterionic surfactants. Typical examples of anionic surfactants are soaps, alkylbenzenesulfonates, alkanesulfonates, olefinsulfonates, alkyl ether sulfonates, glycerol ether sulfonates, α-methyl ester sulfonates, sulfofatty acids, alkyl sulfates, fatty alcohol ether sulfates, glycerol ether sulfates, fatty acid ester sulfates, in particular lauric acid+1EO sulfate, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids, such as, for example, acyl lactylates, acyl tartrates, acyl glutamates and acyl aspartates, alkyl oligoglucoside sulfates, protein fatty acid condensates (in particular vegetable products based on wheat) and alkyl (ether) phosphates. If the anionic surfactants comprise polyglycol ether chains, these can have a conventional homolog distribution, but preferably have a narrowed homolog distribution. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partially oxidized alk(en)yl oligoglycosides and glucuronic acid derivatives, fatty acid N-alkylglucamides, protein hydrolyzates (in particular vegetable products based on wheat), polyol fatty acid esters, sugar esters, sorbitan esters, polysorbates and amine oxides. If the nonionic surfactants comprise polyglycol ether chains, then these can have a conventional homolog distribution, but preferably have a narrowed homolog distribution. Typical examples of cationic surfactants are quaternary ammonium compounds and ester quats, in particular quaternized fatty acid trialkanolamine ester salts. Typical examples of amphoteric or zwitterionic surfactants are alkylbetaines, alkylamidobetaines, aminopropionates, aminoglycinates, imidazoliniumbetaines and sulfobetaines. Said surfactants are exclusively known compounds. With regard to structure and preparation of these substances, reference may be made to relevant review articles, for example, J. Falbe (ed.), "Surfactants in Consumer Products", Springer Verlag, Berlin, 1987, pp. 54–124 or J. Falbe (ed.), "Katalysatoren, Tenside und Mineröladditive" [Catalysts, Surfactants and Mineral Oil Additives], Thieme Verlag, Stuttgart, 1978, pp. 123–217. The proportion of surfactants in the fatty alcohol dispersions can be 0.1 to 10% by weight and preferably 0.5 to 5% by weight.

Fatty Alcohol Dispersions

The fatty alcohol dispersions can be prepared, for example, by the microdispersion method. Microdispersions are optically isotropic, thermodynamically stable systems which comprise a water-insoluble oil component (here: fatty alcohol), dispersants—preferably alkyl glucosides—and water. The clear or transparent appearance of the microdispersions is a consequence of the small particle size of the dispersed emulsion droplets. In this connection, it has been found that fatty alcohol microdispersions have a particularly advantageous effect on the production and storage stability of the resulting coloring preparations. Preference is given to using dispersions which have a particle size of less than 50 μm, in particular of less than 20 μm and particularly preferably less than 10 μm. Reviews on the preparation and use of microdispersions are given by H. Eicke in SÖFW-Journal, 118, 311 (1992) and Th. Förster et al. in SÖFW-Journal, 122, 746 (1996); reference may further be made to the publications DE-A1 4411557 (Henkel) and EP-A1 0687206 (L'Oréal).

Oil Components

Suitable oil components are, for example, Guerbet alcohols based on fatty alcohols having 6 to 18, preferably 8 to 10, carbon atoms, esters of linear $C_6$–$C_{22}$-fatty acids with linear $C_6$–$C_{22}$-fatty alcohols, esters of branched $C_6$–$C_{13}$-carboxylic acids with linear $C_6$–$C_{22}$-fatty alcohols, esters of linear $C_6$–$C_{22}$-fatty acids with branched alcohols, in particular 2-ethylhexanol, esters of linear and/or branched fatty acids with polyhydric alcohols (such as, for example, propylene glycol, dimerdiol or trimertriol) and/or Guerbet alcohols, triglycerides based on $C_6$–$C_{10}$-fatty acids, liquid mono-/di-/triglyceride mixtures based on $C_6$–$C_{18}$-fatty acids, esters of $C_6$–$C_{22}$-fatty alcohols and/or Guerbet alcohols with aromatic carboxylic acids, in particular benzoic acid, esters of $C_2$–$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear $C_6$–$C_{22}$-fatty alcohol carbonates, Guerbet carbonates, esters of benzoic acid with linear and/or branched $C_6$–$C_{22}$-alcohols (e.g. Finsolv® Tennessee), dialkyl ethers, ring-opening products of epoxidized fatty acid esters with polyols, silicone oils and/or aliphatic or naphthenic hydrocarbons.

Hair Dyes

Suitabe hair dyes are in this connection, for example, direct dyes, e.g. from the group of nitrophenylenediamines, nitroaminophenols, anthraquinones or indophenols, such as, for example, the compounds known under the international names or trade names HC Yellow 2, HC Yellow 4, Basic Yellow 57, Disperse Orange 3, HC Red 3, HC Red BN, Basic Red 76, HC Blue 2, Disperse Blue 3, Basic Blue 99, HC Violet 1, Disperse Violet 1, Disperse Violet 4, Disperse Black 9, Basic Brown 16, Basic Brown 17, picramic acid and Rodol 9 R, and also 4-amino-2-nitrodiphenylamine-2'-carboxylic acid, 6-nitro-1,2,3,4-tetrahydroquinoxaline, (N-2,3-di-hydroxypropyl-2-nitro-4-trifluoromethyl) aminobenzene and 4-N-ethyl-1,4-bis(2'-hydroxyethylamino)-2-nitrobenzene hydrochloride. Furthermore, it is also possible to add to the emulsions naturally occuring dyes, such as, for example, henna red, henna neutral, henna black, camomile blossoms, sandalwood, black tea, buckthorn bark, sage, logwood, madder root, catechu, sedre and alkanna root.

As well as the direct dyes, oxidation dyes, consisting of developer and coupler component, can also be added to the emulsions. The developer components used are, for example, primary aromatic amines having a further free or substituted hydroxyl or amino group situated in the para- or ortho-position, diaminopyridine derivatives, heterocyclic hydrazones, 4-aminopyrazolone derivatives, and 2,4,5,6-tetraaminopyrimidine and derivatives thereof. Specific representatives include p-toluylenediamine, p-aminophenol, N,N-bis(2-hydroxyethyl)-p-phenylenediamine, 2-(2,5-diaminophenoxy)ethanol, 1-phenyl-3-carboxyamido-4-amino-5-pyrazolone and 4-amino-3-methylphenol, 2-(2-hydroxyethyl)-1,4-amino-benzene and 2,4,5,6-tetraaminopyrimidine. The coupler components used are generally m-phenylenediamine derivatives, naphthols, resorcinol and resorcinol derivatives, pyrazolones, m-aminophenols, and pyridine derivatives. Suitable coupler substances are, in particular, 1-naphthol, pyrogallol, 1,5-, 2,7- and 1,7-dihydroxynaphthalene, 5-amino-2-methylphenol, m-aminophenol, resorcinol, resorcinol-monomethyl ether, m-phenylenediamine, 1-phenyl-3-methyl-5-pyrazolone, 2,4-dichloro-3-aminophenol, 1,3-bis(2,4-diaminophenoxy)propane, 2-chlororesorcinol, 2-chloro-6-methyl-3-aminophenol, 2-methylresorcinol, 2,5-dimethyl-resorcinol, 2,6-dihydroxypyridine and 2,6-diaminopyridine.

As regards further dye components, reference is made expressly to the Colipa list, published by the Industrieverband Körperpflege und Waschmittel [Industrial Association for Body Care and Detergents], Frankfurt. A review of suitable dyes is further given in the publication "Kosmetische Färbemittel" [Cosmetic Colorants] from the Farbstoffkommission der Deutschen Forschungsgemeinschaft [Dyes Commission of the German Research Society], Verlag Chemie, Weinheim, 1984, pp. 81–106. The hair colors can be present in amounts of from 0.1 to 15% by weight, preferably 0.5 to 10% by weight and in particular 1 to 5% by weight, based on the hair coloring preparations.

Polymeric Thickeners

In a further preferred embodiment of the invention, as well as comprising the surface-active fatty alcohol dispersions, the hair coloring preparations comprise polymeric thickeners, such as, for example, polysaccha-rides, in particular xanthan gum, guar guar, agar agar, alginates and tyloses, carboxymethyl-cellulose and hydroxyethylcellulose, and also relatively high molecular weight polyethylene glycol mono- and diesters of fatty acids, polyacrylates, (e.g. Carbopole® from Goodrich or Synthalene® from Sigma), polyacrylamides, polyvinyl alcohol and polyvinylpyrrolidone. The polymers can be used in amounts of from 0.1 to 5% by weight, preferably 0.5 to 2% by weight, based on the hair coloring preparation.

Industrial Applicability

Using the surface-active fatty alcohol dispersions it is possible to produce, also by a cold method, i.e. at temperatures in the range from 18 to 25° C., hair coloring preparations which are in the form of lamellar gels. The invention therefore further relates to the uses of surface-active fatty alcohol dispersions, preferably fatty alcohol microdispersions, as bodying agents for the production of hair coloring preparations, preferably of O/W coloring creams, in which they may be present in amounts of from 10 to 70% by weight and preferably 25 to 35% by weight.

Further Auxiliaries and Additives

The hair coloring preparations according to the invention are preferably O/W creams, which may comprise, as further auxiliaries and additives, co-emulsifiers, superfatty agents, pearlescent waxes, stabilizers, further bodying agents, electrolyte salts, cationic polymers, silicone compounds, biogenic active ingredients, antidandruff agents, film formers, preservatives, hydrotropic agents, solubilizers, UV light protection filters, perfume oils and the like.

The surfactants present in the fatty alcohol dispersions which act therein as dispersants can likewise serve as emulsifiers in the end preparations. In addition, it is also possible to add other surfactants or co-emulsifiers to the hair coloring preparations, such as, for example:

(1) addition products of from 2 to 30 mol of ethylene oxide and/or 0 to 5 mol of propylene oxide to linear fatty alcohols having 8 to 22 carbon atoms, to fatty acids having 12 to 22 carbon atoms and to alkylphenols having 8 to 15 carbon atoms in the alkyl group;

(2) $C_{12/18}$-fatty acid mono- and diesters of addition products of from 1 to 30 mol of ethylene oxide to glycerol;

(3) glycerol mono- and diesters and sorbitan mono- and diesters of saturated and unsaturated fatty acids having 6 to 22 carbon atoms and the ethylene oxide addition products thereof;

(4) alkyl mono- and oligoglycosides having 8 to 22 carbon atoms in the alkyl radical and the ethoxylated analogs thereof;

(5) addition products of from 15 to 60 mol of ethylene oxide to castor oil and/or hydrogenated castor oil;

(6) polyol and, in particular, polyglycerol esters, such as, for example, polyglycerol polyricinoleate, polyglycerol poly-12-hydroxystearate or polyglycerol dimerate. Likewise suitable are mixtures of compounds from two or more of these classes of substance;

(7) addition products of from 2 to 15 mol of ethylene oxide to castor oil and/or hydrogenated castor oil;

(8) partial esters based on linear, branched, unsaturated or saturated $C_{6/22}$-fatty acids, ricinoleic acid, and 12-hydroxystearic acid and glycerol, polyglyerol, pentaerythritol, dipentaerythritol, sugar alcohols (e.g. sorbitol), alkyl glucosides (e.g. methyl glucoside, butyl glucoside, lauryl glucoside), and polyglucosides (e.g. cellulose);

(9) mono-, di- and trialkyl phosphates, and mono-, di- and/or tri-PEG alkyl phosphates;

(10) woolwax alcohols;

(11) polysiloxane-polyalkyl-polyether copolymers and corresponding derivatives;

(12) mixed esters of pentaerythritol, fatty acids, citric acid and fatty alcohol as in German Patent 1165574 and/or mixed esters of fatty acids having 6 to 22 carbon atoms, methylglucose and polyols, preferably glycerol, and

(13) polyalkylene glycols.

The addition products of ethylene oxide and/or of propylene oxide to fatty alcohols, fatty acids, alkylphenols, glycerol mono- and diesters, and sorbitan mono- and diesters of fatty acids or of castor oil are known, commercially available products. These are homolog mixtures whose average degree of alkoxylation corresponds to the ratio of the amounts of ethylene oxide and/or propylene oxide and substrate with which the addition reaction is carried out. $C_{12/18}$-fatty acid mono- and diesters of addition products of ethylene oxide to glycerol are known from German Patent 20 24 051 as refatting agents for cosmetic preparations.

$C_{8/18}$-Alkyl mono- and oligoglycosides, their preparation and their use are known from the prior art. They are prepared, in particular, by reacting glucose or oligosaccharides with primary alcohols having 8 to 18 carbon atoms. As regards the glycoside radical, both monoglycosides, in which a cyclic sugar radical is bonded glycosidically to the fatty alcohol, and also oligomeric glycosides having a degree of oligomerization up to, preferably, about 8 are suitable. The degree of oligomerization is a statistical average value which is based on a homolog distribution customary for such technical-grade products.

Furthermore, the emulsifiers used can be zwitterionic surfactants. The name zwitterionic surfactants is used for those surface-active compounds which carry at least one quaternary ammonium group and at least one carboxylate and a sulfonate group in the molecule. Particularly suitable zwitterionic surfactants are the so-called betaines, such as N-alkyl-N,N-dimethylammonium glycinate, for example cocoalkyldimethylammonium glycinate, N-acylaminopropyl-N,N-dimethylammonium glycinate, for example cocoacylaminopropyldimethylammonium glycinate, and 2-alkyl-3-carboxymethyl-3-hydroxyethylimidazolines having in each case 8 to 18 carbon atoms in the alkyl or acyl group, and cocoacylaminoethylhydroxyethylcarboxymethyl glycinate. Particular preference is given to the fatty acid amide derivative known under the CTFA name *Cocamidopropyl Betaine*. Likewise suitable emulsifiers are ampholytic surfactants. The term "ampholytic surfactants" means those surface-active compounds which, apart from a $C_{8/18}$-alkyl or -acyl group in the molecule, contain at least one free amino group and at least one —COOH— or —SO$_3$H— group and are able to form internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case about 8 to 18 carbon atoms in the alkyl group. Particularly preferred ampholytic surfactants are N-cocoalkylaminopropionate, cocoacylaminoethylaminopropionate and $C_{12/18}$-acylsarcosine. As well as the ampholytic emulsifiers, quaternary emulsifiers are also suitable, those of the ester quat type, preferably methylquaternized difatty acid triethanolamine ester salts, being particularly preferred.

The superfatting agents used may be substances such as, for example, lanolin and lecithin, and polyethoxylated or acylated lanolin and lecithin derivatives, polyol fatty acid esters, monoglycerides and fatty acid alkanolamides, the latter also serving as foam stabilizers.

Examples of suitable pearlescent waxes are: alkylene glycol esters, specifically ethylene glycol distearate; fatty acid alkanolamides, specifically coconut fatty acid diethanolamide; partial glycerides, specifically stearic acid monoglyceride; esters of polyhydric, optionally hydroxy-substituted carboxylic acids with fatty alcohols having 6 to 22 carbon atoms, specifically long-chain esters of tartaric acid; fatty substances, such as, for example, fatty alcohols, fatty ketones, fatty aldehydes, fatty ethers and fatty carbonates which have a total of at least 24 carbon atoms, specifically laurone and distearyl ether; fatty acids, such as stearic acid, hydroxystearic acid or behenic acid, ring-opening products of olefin epoxides having 12 to 22 carbon atoms with fatty alcohols having 12 to 22 carbon atoms and/or polyols having 2 to 15 carbon atoms and 2 to 10 hydroxyl groups, and mixtures thereof.

As well as the fatty alcohols, other suitable bodying agents are partial glycerides in particular. Preference is given to a combination of these substances with alkyl oligoglucosides and/or fatty acid N-methylglucamides of identical chain length and/or polyglycerol poly-12-hydroxystearate.

Examples of suitable cationic polymers are cationic cellulose derivatives, such as, for example, a quaternized hydroxyethylcellulose obtainable under the name Polymer JR 400® from Amerchol, cationic starch, copolymers of diallylammonium salts and acrylamides, quaternized vinylpyrrolidone/vinylimidazole polymers, such as, for example, Luviquat® (BASF), condensation products of polyglycols and amines, quaternized collagen polypeptides, such as, for example, lauryldimonium hydroxypropyl hydrolyzed collagen (Lamequat®L/Grünau), quaternized wheat polypeptides, polyethyleneimine, cationic silicone polymers, such as, for example, amidomethicones, copolymers of adipic acid and dimethylaminohydroxypropyldiethylenetriamine (Cartaretine®/Sandoz), copolymers of acrylic acid with dimethyldiallylammonium chloride (Merquat® 550/Chemviron), polyaminopolyamides, as described, for example, in FR-A 2252840, and crosslinked water-soluble polymers thereof, cationic chitin derivatives, such as, for example, quaternized chitosan, optionally microcrystalline-dispersed, condensation products of dihaloalkylene, such as, for example, dibromobutane with bisdialkylamines, such as, for example, bis-dimethylamino-1,3-propane, cationic guar gum, such as, for example, Jaguar® CBS, Jaguar® C-17, Jaguar® C-16 from Celanese, quaternized ammonium salt polymers, such as, for example, Mirapol® A-15, Mirapol® AD-1, Mirapol® AZ-1 from Miranol.

Examples of suitable silicone compounds are dimethylpolysiloxanes, methylphenylpolysiloxanes, cyclic silicones, and amino-, fatty-acid-, alcohol-, polyether-, epoxy-, fluorine-, glycoside- and/or alkyl-modified silicone compounds, which can either be liquid or in resin form at room temperature. Typical examples of fats are glycerides, and suitable waxes are inter alia beeswax, carnauba wax, candelilla wax, montan wax, paraffin wax or microcrystalline waxes, optionally in combination with hydrophilic waxes, e.g. cetylstearyl alcohol or partial glycerides. Stabilizers which can be used are metal salts of fatty acids, such as, for example, magnesium, aluminum and/or zinc stearate. The term biogenic active ingredients means, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes. The antidandruff agents used may be climbazole, octopirox and zinc pyrethione. Customary film formers are, for example, chitosan, microcrystalline chitosan, quaternized chitosan, polyvinylpyrrolidone, vinylpyrrolidone-vinyl acetate copolymers, polymers of the acrylic acid series, quaternary cellulose derivatives, collagen, hyaluronic acid and salts thereof, and similar compounds. Possible swelling agents for aqueous phases are montmorillonites, clay mineral substances, Pemulen, and alkyl-modified Carbopol grades (Goodrich).

The term "UV light protection filters" are organic substances which are able to absorb ultraviolet rays and give off the absorbed energy again in the form of longer-wavelength radiation, e.g. heat. UVB filters can be oil-soluble or water-soluble. Examples of oil-soluble substances are:

3-benzylidenecamphor and derivatives thereof, e.g. 3-(4-methylbenzylidene)camphor;

4-aminobenzoic acid derivatives, preferably 2-ethylhexyl 4-(dimethylamino)benzoate, 2-octyl 4-(dimethylamino)benzoate and amyl 4-(dimethylamino)benzoate;

esters of cinnamic acid, preferably 2-ethylhexyl 4-methoxycinnamate, isopentyl 4-methoxycinnamate, 2-ethylhexyl 2-cyano-3-phenylcinnamate (octocrylene);

esters of salicylic acid, preferably 2-ethylhexyl salicylate, 4-isopropylbenzyl salicylate, homomenthyl salicylate;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably di-2-ethylhexyl 4-methoxybenzylmalonate;

triazine derivatives, such as, for example, 2,4,6-trianilino (p-carbo-2'-ethyl-1'-hexyloxy)-1,3,5-tri-azine and octyltriazone, propane-1,3-diones, such as, for example, 1-(4-tert-butylphenyl)-3-(4'-methoxyphenyl)propane-1,3-dione.

Suitable water-soluble substances are:

2-phenylbenzimidazole-5-sulfonic acid and the alkali metal, alkaline earth metal, ammonium, alkylammonium, alkanolammonium and glucammonium salts thereof;

sulfonic acid derivatives of benzophenones, preferably 2-hydroxy-4-methoxybenzophenone-5-sulfonic acid and its salts;

sulfonic acid derivatives of 3-benzylidenecamphor, such as, for example, 4-(2-oxo-3-bornylidenemethyl)-benzenesulfonic acid and 2-methyl-5-(2-oxo-3-bornylidene)sulfonic acid and salts thereof.

Suitable typical UV-A filters are, in particular, derivatives of benzoylmethane, such as, for example, 1-(4'-tert-butylphenyl)-3-(4'-methoxyphenyl)propane-1,3-dione or 1-phenyl-3-(4'-isopropylphenyl)propane-1,3-dione. The UV-A and UV-B filters can of course also be used in mixtures. As well as said soluble substances, insoluble pigments, namely finely disperse metal oxides or salts, are also suitable for this purpose, such as, for example, titanium dioxide, zinc oxide, iron oxide, aluminum oxide, cerium oxide, zirconium oxide, silicates (talc), barium sulfate and zinc stearate. The particles should here have an average diameter of less than 100 nm, preferably between 5 and 50 nm, and in particular between 15 and 30 nm. They can have a spherical shape, although it is also possible to use particles which have an ellipsoid shape or a shape deviating in some other way from the spherical form. As well as the two abovementioned groups of primary light protection substances, it is also possible to use secondary light protection agents of the antioxidant type, which interrupt the photochemical reaction chain which is triggered when UV radiation penetrates the skin. Typical examples thereof are superoxide dismutase, tocopherols (vitamin E) and ascorbic acid (vitamin C). Other suitable UV light protection filters are given in the review by P. Finkel in SÖFW-Journal 122, 543 (1996).

To improve the flow behavior, it is also possible to use hydrotropic agents, such as, for example, ethanol, isopropyl alcohol, or polyols. Polyols which are suitable here preferably have 2 to 15 carbon atoms and at least two hydroxyl groups. Typical examples are glycerol;

alkylene glycols, such as, for example, ethylene glycol, diethylene glycol, propylene glycol, butylene glycol, hexylene glycol, and polyethylene glycols having an average molecular weight of from 100 to 1000 daltons;

technical-grade oligoglycerol mixtures having a degree of autocondensation of from 1.5 to 10, such as, for example, technical-grade diglycerol mixtures with a diglycerol content of from 40 to 50% by weight;

methylol compounds, such as, in particular, trimethylolethane, trimethylolpropane, trimethylolbutane, pentaerythritol and dipentaerythritol;

lower alkyl glucosides, in particular those with 1 to 8 carbon atoms in the alkyl radical, such as, for example, methyl and butyl glucoside;

sugar alcohols having 5 to 12 carbon atoms, such as, for example, sorbitol or mannitol, sugars having 5 to 12 carbon atoms, such as, for example, glucose or sucrose;

amino sugars, such as, for example, glucamine.

Examples of suitable preservatives are phenoxyethanol, formaldehyde solution, parabens, pentanediol or sorbic acid.

Perfume oils which may be mentioned are extracts from flowers (lavender, rose, jasmine, neroli), stems and leaves (geranium, patchouli, petitgrain), fruits (aniseed, coriander, cumin, juniper), fruit peels (bergamot, lemon, orange), roots (mace, angelica, celery, cardamon, costus, iris, calmus), woods (sandalwood, guaiac wood, cedarwood, rosewood), herbs and grasses (taragon, lemon grass, sage, thyme), needles and branches (spruce, fir, pine, dwarf-pine), resins and balsams (galbanum, elemi, benzoin, myrrh, olibanum, opoponax). Animal raw materials are also suitable, such as, for example, musk, civet and castoreum. Suitable synthetic or semisynthetic perfume oils are ambroxan, eugenol, isoeugenol, citronellal, hydroxycitronellal, geraniol, citronellol, geranyl acetate, citral, ionone and methylionone.

EXAMPLES

Examples 1 to 4, Comparative Example V1

To prepare the creams 1 to 4 according to the invention, an approximately 30% strength by weight dispersion of cetylstearyl alcohol in water was used in each case which comprised, as stabilizers, 1% by weight—based on the dispersion—of each of sodium lauryl sulfate (D1), sodium laureth sulfate (D2) and coco glucosides (D3, D4). The dispersions were prepared by the micro-dispersion technique. Dispersion D1 had an average particle size of 55 $\mu$m, dispersions D2 and D3 of 40 $\mu$m, and dispersion D4 of 10 $\mu$m. In the case of the comparative cream V1, the cetylstearyl alcohol was stirred in directly, i.e. not as an aqueous surface-active dispersion. The five O/W creams were prepared by homogenizing the components at 20° C. The viscosity was determined directly and after storage for a period of 4 weeks at 40° C., using the Brookfield method (10 rpm, spindle 1). The results are given in Table 1:

TABLE 1

Viscosity and stability of O/W hair coloring creams - amounts given as % by weight of active substance

| Composition/ performance | 1 | 2 | 3 | 4 | V1 |
|---|---|---|---|---|---|
| Fatty alcohol dispersion D1 | 20.0 | — | — | — | — |
| Fatty alcohol dispersion D2 | — | 20.0 | — | — | — |
| Fatty alcohol dispersion D3 | — | — | 20.0 | 20.0 | — |
| Cetearyl alcohol | — | — | — | — | 20.0 |
| Ammonia | 2.0 | 2.0 | 2.0 | 2.0 | 2.0 |
| Ammonium chloride | 0.5 | 0.5 | 0.5 | 0.5 | 0.5 |
| Tetrasodium EDTA | 0.5 | 0.5 | 0.5 | 0.5 | 0.5 |
| Coco glucosides | 5.0 | 5.0 | 5.0 | 5.0 | 5.0 |
| Hydroxycetyl hydroxyethyl dimonium chloride | 1.0 | 1.0 | 1.0 | 1.0 | 1.0 |
| Oleic acid | 2.5 | 2.5 | 2.5 | 2.5 | 2.5 |
| Sodium sulfite | 1.0 | 1.0 | 1.0 | 1.0 | 1.0 |
| N,N'-bis(4-aminophenyl)-piperidine | 5.0 | 5.0 | 5.0 | 5.0 | 5.0 |
| Resorcinol | 5.0 | 5.0 | 5.0 | 5.0 | 5.0 |
| Water | | | | ad 100 | |
| Viscosity [mpas] | | | | | |
| immediately | 12,000 | 12,500 | 12,500 | 13,000 | 9,000 |
| after 4 weeks (40° C.) | 11,500 | 12,000 | 12,000 | 13,000 | — |
| Stability after 4 weeks (40° C.) | stable | stable | stable | stable | 2-phase |

What is claimed is:

1. A process for making a hair dye preparation comprising:
   (a) providing an aqueous surface-active fatty alcohol dispersion containing:
      (i) a fatty alcohol; and
      (ii) a surfactant;
   (b) stirring said dispersion with an oil component; and
   (c) a hair dye component at a temperature of from 18 to 25° C., to form the hair dye preparation.

2. The process of claim 1 wherein the fatty alcohol is present in the fatty alcohol dispersion in an amount of from 5 to 50% by weight, based on the weight of the fatty alcohol dispersion.

3. The process of claim 1 wherein the surfactant is present in the fatty alcohol dispersion in an amount of from 0.1 to 10% by weight, based on the weight of the fatty alcohol dispersion.

4. The process of claim 1 wherein the aqueous surface-active fatty alcohol dispersion has a particle size of less than 50 $\mu$m.

5. The process of claim 1 wherein the aqueous surface-active fatty alcohol dispersion is present in the hair dye preparation in an amount of from 10 to 70% by weight, based on the weight of the hair dye preparation.

6. The process of claim 1 wherein the hair dye preparation further contains a polymeric thickener.

7. The process of claim 6 wherein the polymeric thickener is present in the hair dye preparation in an amount of from 0.1 to 5% by weight, based on the weight of the preparation.

8. A process for coloring hair comprising
   (a) providing an aqueous surface-active fatty alcohol dispersion containing:
      (i) a fatty alcohol; and (ii) a surfactant;
   (b) stirring said dispersion with an oil component and a hair dye component at a temperature of from 18 to 25° C., to form a hair dye preparation; and
   (c) contacting the hair with said hair dye preparation.

9. The process of claim 8 wherein the fatty alcohol is present in the fatty alcohol dispersion in an amount of from 5 to 50% by weight, based on the weight of the fatty alcohol dispersion.

10. The process of claim 8 wherein the surfactant is present in the fatty alcohol dispersion in an amount of from 0.1 to 10% by weight, based on the weight of the fatty alcohol dispersion.

11. The process of claim 8 wherein the aqueous surface-active fatty alcohol dispersion has a particle size of less than 50 $\mu$m.

12. The process of claim 8 wherein the aqueous surface-active fatty alcohol dispersion is present in the hair dye preparation in an amount of from 10 to 70% by weight, based on the weight of the hair dye preparation.

13. The process of claim 8 wherein the hair dye preparation further contains a polymeric thickener.

14. The process of claim 13 wherein the polymeric thickener is present in the hair dye preparation in an amount of from 0.1 to 5% by weight, based on the weight of the preparation.

* * * * *